United States Patent
Duan et al.

(10) Patent No.: US 10,626,079 B2
(45) Date of Patent: Apr. 21, 2020

(54) METHOD FOR PREPARING SINGLE CRYSTAL OF ANHYDROUS HALOGENATED CHOLINE OR DERIVATIVE THEREOF

(71) Applicant: HEBEI UNIVERSITY OF SCIENCE AND TECHNOLOGY, Hebei (CN)

(72) Inventors: Erhong Duan, Hebei (CN); Shaohan Lian, Hebei (CN); Zidan Chen, Hebei (CN); Hongwei Ren, Hebei (CN); Hua Sun, Hebei (CN); Jianrui Niu, Hebei (CN)

(73) Assignee: HEBEI UNIVERSITY OF SCIENCE AND TECHNOLOGY (CN)

( * ) Notice: Subject to any disclaimer, the term of this patent is extended or adjusted under 35 U.S.C. 154(b) by 0 days.

(21) Appl. No.: 16/329,120

(22) PCT Filed: Apr. 28, 2017

(86) PCT No.: PCT/CN2017/082502
§ 371 (c)(1),
(2) Date: Feb. 27, 2019

(87) PCT Pub. No.: WO2018/195956
PCT Pub. Date: Nov. 1, 2018

(65) Prior Publication Data
US 2020/0039918 A1 Feb. 6, 2020

(30) Foreign Application Priority Data
Apr. 27, 2017 (CN) .......................... 2017 1 0284716

(51) Int. Cl.
*C07C 213/10* (2006.01)

(52) U.S. Cl.
CPC ........ *C07C 213/10* (2013.01); *C07B 2200/13* (2013.01)

(58) Field of Classification Search
CPC ........................... C07C 213/00; C07B 200/13
USPC ........................................................ 560/248
See application file for complete search history.

(56) References Cited

U.S. PATENT DOCUMENTS

| 2002/0161039 A1 | 10/2002 | Volkel et al. .................. 514/474 |
| 2009/0182039 A1 | 7/2009 | Imamura et al. ............. 514/460 |
| 2013/0345464 A1 | 12/2013 | Oh et al. |

FOREIGN PATENT DOCUMENTS

| CN | 103936624 | | 7/2014 | .......... C07C 269/00 |
| CN | 103936624 A | * | 7/2014 | |
| CN | 104628564 | | 5/2015 | .......... C07C 213/10 |
| CN | 105198761 | | 12/2015 | .......... C07C 213/06 |
| CN | 105198761 A | * | 12/2015 | |

(Continued)

OTHER PUBLICATIONS

International Search Report (w/translation) and Written Opinion (no translation) issued in application No. PCT/CN2017/082502, dated Jan. 23, 2018 (10 pgs).

*Primary Examiner* — Deborah D Carr
(74) *Attorney, Agent, or Firm* — Hayes Soloway P.C.

(57) ABSTRACT

Disclosed is a method for preparing high-quality anhydrous choline halide single crystal and its derivatives. The single crystal product has good stability of light and heat. It also has the advantages of moisture resistant, deliquescent resistance and is not easy to agglomerate. The method is simple in operation. The solvent used in the process is difficult to volatilize and can be recycled.

9 Claims, 3 Drawing Sheets the crystal structure of anhydrous choline chloride single crystal

(56) References Cited

FOREIGN PATENT DOCUMENTS

| | | | | |
|---|---|---|---|---|
| CN | 105254515 | | 1/2016 | ........... C07C 213/06 |
| CN | 105254515 A | * | 1/2016 | |
| DE | 10109073 | | 9/2002 | ........... A23K 20/105 |
| WO | WO2007007628 | | 1/2009 | ........... A61K 31/351 |
| WO | WO2012124907 | | 9/2012 | ............. C07B 61/00 |

* cited by examiner

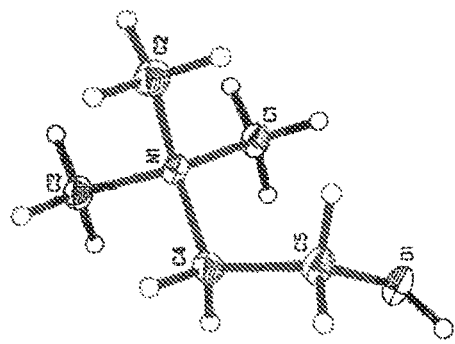
Figure 1 the crystal structure of anhydrous choline chloride single crystal
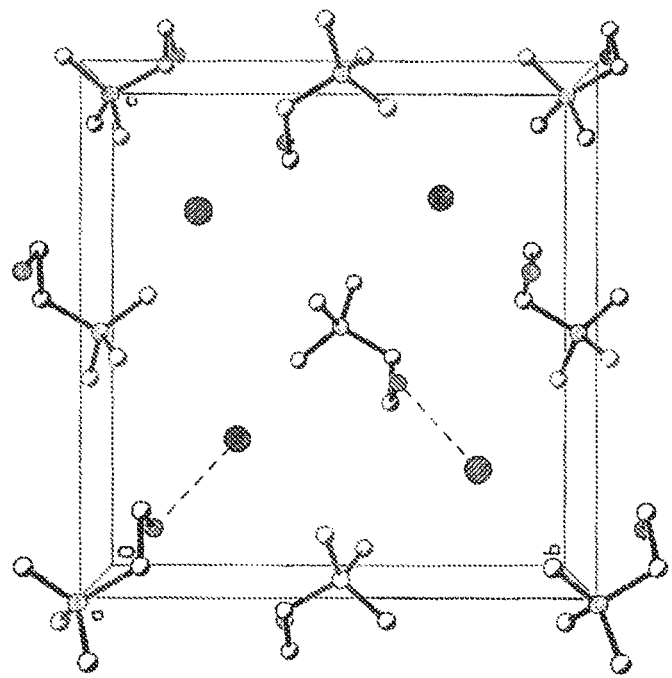
Figure 2 Cell diagram of anhydrous choline chloride single crystal

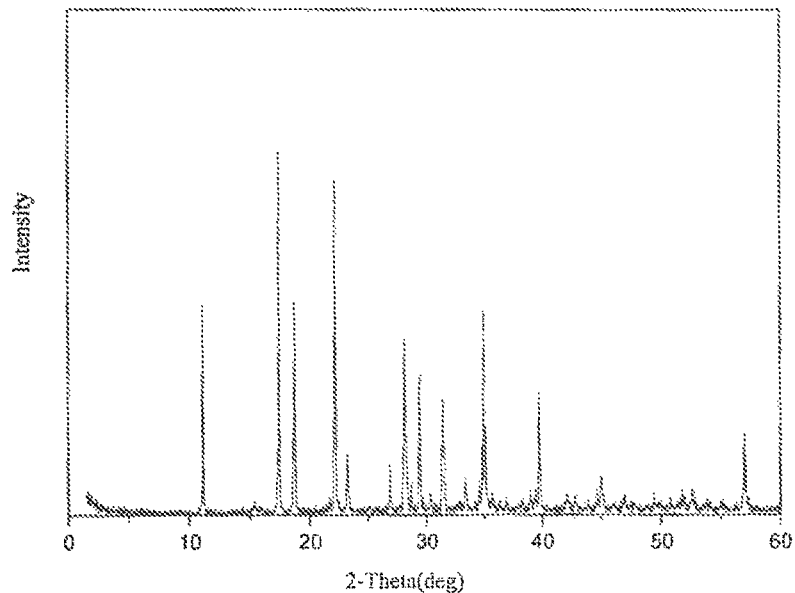
Figure 3 XRD of anhydrous choline chloride single crystal
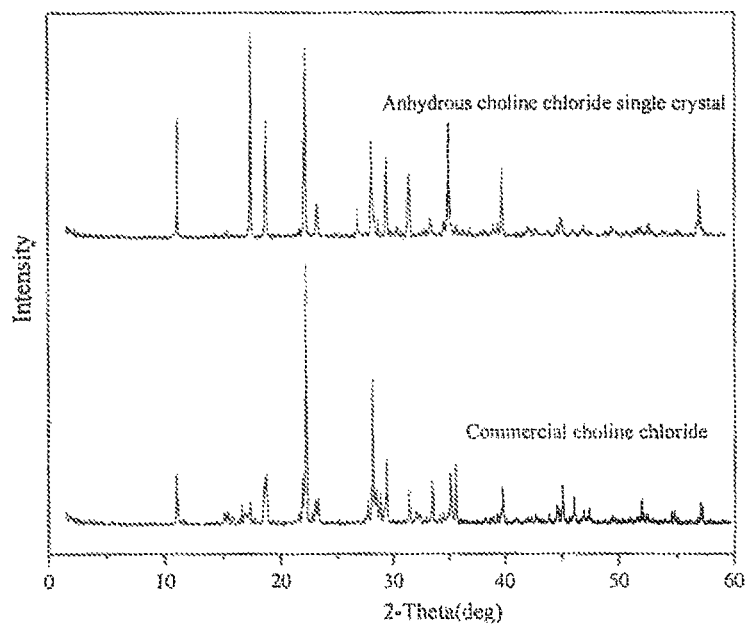
Figure 4 XRD of anhydrous choline chloride single crystal and commercial choline chloride

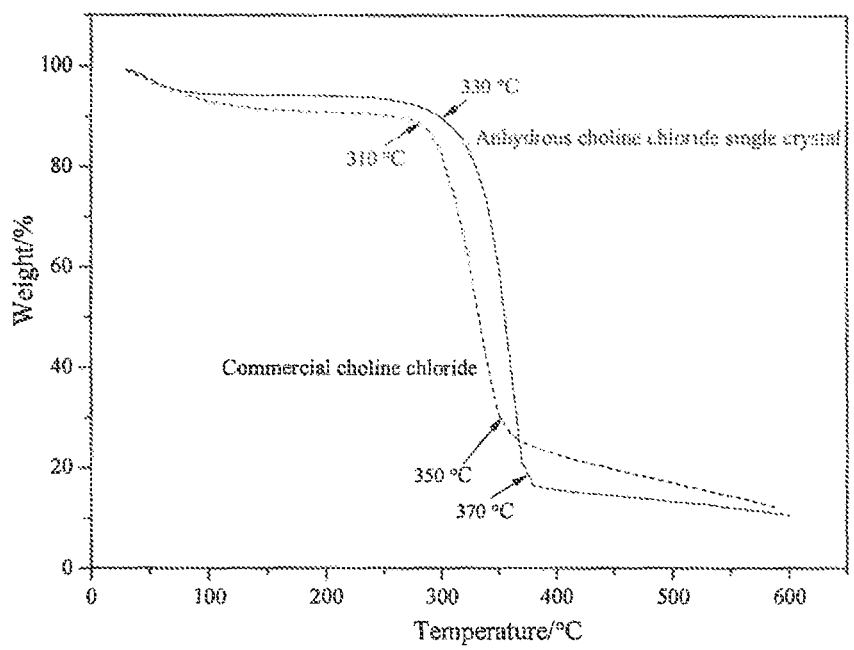
Figure 5 TG of anhydrous choline chloride single crystal and commercial choline chloride

METHOD FOR PREPARING SINGLE CRYSTAL OF ANHYDROUS HALOGENATED CHOLINE OR DERIVATIVE THEREOF

TECHNICAL FIELD

The invention belongs to the field of chemistry, and it provides a new method to prepare anhydrous choline halide single crystal and its derivatives.

BACKGROUND TECHNIQUES

Choline halide and its derivatives are important raw material, and have been applied in many fields. Choline halide and its derivatives (such as choline chloride, choline bromide, choline iodide, and acetylcholine chloride, etc.) are a kind of common feed additives in the breeding industry, which can stimulate egg production and weight gain. It is a plant photosynthesis promoter in the crop industry and has a significant effect on the increasing of yield. It can be used to treat fatty liver and cirrhosis in the pharmaceutical industry, especially animal medicine. It is also an important raw material for synthesizing organic chemical products in the chemical industry.

The single crystal product has good stability of light and heat. It has the advantages of moisture resistant, deliquescent resistance and is not easy to agglomerate too. High-quality choline halide and its derivatives are the guarantee for the synthesis of high-quality products. At present, the commercial choline halide and its derivatives products are mostly polycrystalline crystal or crystal powders. They are easily to deliquescent, agglomerate or be color changed, thus greatly shorten the storage cycle and reducing the quality of the product. It brings many inconveniences in the application. Single crystal is the pure product with strict internal atom arrangement, so it has great advantages in mechanics, optics, thermal, chemical activity and chemical stability. Nowadays, single crystal has been widely used in many fields, especially in the high-technology industry, and the demand for single crystal product is increasing. However, single crystal in nature is far from meeting the needs of human development, and it is urgent to develop the artificial culture of single crystal. The traditional solvent-evaporation method has many drawbacks, such as large-random product quality, difficult-control production process, unpredictable production cycle, and restricted production scale.

SUMMARY OF THE INVENTION

There are many technical problems in traditional solvent-evaporation method, such as large-random product quality, difficult-control production process, unpredictable production cycle, and restricted production scale. To solve the problems, the present invention provides a new method to prepare anhydrous choline halide single crystal and its derivatives.

To achieve the above object, the present invention adopts the following technical solutions: The invention provides a new method to prepare anhydrous choline halide single crystal and its derivatives, and it includes the following steps:

(1) Choline halide or its derivative, alcohol-ether compound (they can form binary system) or mixture of alcohol-ether compound and polyol (they can form ternary system) are weighed precisely at an optimal molar ratio.

(2) Alcohol-ether compound or mixture of alcohol-ether compound and polyol are added into the reactor with stirring, and heated to 70~90° C. Then, choline halide or its derivative is also added into the reactor to react with the former raw materials. The reaction lasts until the homogeneous liquid phase (deep eutectic solvent, DES) is formed.

(3) The DES product is cooled to 15° C., and then maintained at 15° C. for a period of time until no more single crystal is precipitated.

(4) After filtration, washing, and vacuum drying, anhydrous choline halide single crystal or its derivative product is obtained.

Further, the chemical formula of anhydrous choline halide single crystal and its derivatives in Step (4) is as follows: $R_1R_2R_3NCH_2CH_2OR_4^+X^-$, wherein $R_1$ means methyl or ethyl, $R_2$ means methyl or ethyl, $R_3$ means methyl, ethyl, propyl or butyl, $R_4$ means hydrogen, acetyl, propionyl or butyryl, and X means chlorine, bromine or iodine.

Further, the chemical formula of alcohol-ether compound is as follows: $HO(CH_2)_nOR$ or its isomer, wherein n is an integer of 1 to 10, and R means methyl group, ethyl group, propyl group, or butyl.

Further, the chemical formula of polyol in Step (1) is as follows: $HO(CH_2)_nOR$ or polyethylene glycol, wherein n is an integer of 1 to 10.

Further, the optimal moral ratio of raw materials in Step (1) is $n_{calcohol-ether\ compound\ or\ mixture\ of\ alcohol-ether\ compound\ and\ polyol} : n_{choline\ halide\ or\ its\ derivative} = 1:3$.

Further, the optimal moral ratio of mixture of alcohol-ether compound and polyol in Step (1) is $n_{alcohol-ether\ compound} : n_{polyol} = 1:3$.

Further, the characteristics of the preparation method are: the reaction time in Step (2) is 40~90 min.

Further, the temperature in the step (3) is controlled by cooling program. The temperature is reduced 0.2 to 0.6° C./min in the range of 90 to 70° C., 0.6 to 1.2° C./min in the range of 70 to 55° C., and 1.2~1.5° C./min the range of 55 to 15° C. To optimize, the temperature in the step (3) is controlled by cooling program. The temperature is reduced 0.5° C./min in the range of 90 to 70° C., 0.9° C./min in the range of 70 to 55° C., and 1.2° C./min in the range of 55 to 15° C.

The invention provides a new method to prepare anhydrous choline halide single crystal and its derivative by deep eutectic solvent method. Considering the physical and chemical properties of the raw materials, the anhydrous choline halide single crystals and its derivative are successfully prepared by optimizing the process conditions of dissolution temperature, crystallization rate and reactant ratio. The temperature of dissolution and crystallization affects both the quality of single crystal product and the yield of the product.

Taking choline chloride as an example, the crude choline chloride is insoluble in ether and ethylene glycol monomethyl ether at room temperature. However, a uniform transparent deep eutectic solvent can be formed after heated in 70~90° C. water baths for 1 to 3 hours. The anhydrous choline chloride single crystal is precipitated by cooling program. During the cooling process, the temperature-reducing rate is very important. Too fast temperature-reducing rate would lead to poor-quality single crystal or even no product produced. Too fast temperature-reducing rate would result in insufficient driving force and inefficiency production.

The optimized cooling program for preparing anhydrous choline chloride single crystal is as follows: 0.5° C./min in the range of 90~70° C., 0.9° C./min in the range of 70~55° C., and 1.2° C./min in the range of 55~15° C. The moral ratio of raw materials has great effect on the chemical reaction and chemical stability of reactants. The optimized moral ratio of raw materials is as follows: The amount of alcohol-ether compound or mixture of alcohol-ether compound and polyol is 1 to 3 times that of choline halide or its derivative, wherein the moral ratio of the amount of alcohol ether compound to polyol is 1:1 to 1:3.

Advantages and Benefits of the Present Invention

The invention provides a new environment-friendly method to prepare anhydrous choline halide single crystal and its derivative from deep eutectic solvent under the mild condition. The single crystal product has good stability of light and heat. It also has the advantages of moisture resistant, deliquescent resistance and is not easy to agglomerate. The production process is simple in operation which can greatly reduce the production cost. The solvent used in the process is difficult to volatilize and can be recycled. In summary, the invention provides a new method to prepare anhydrous choline halide single crystal and its derivative. It has good economic, environmental and social benefits.

INSTRUCTION OF DRAWINGS

The invention will be further instructed in detail with reference to the appendix figures and experiment examples.

FIG. 1 The crystal structure of anhydrous choline chloride single crystal;

FIG. 2 Cell diagram of anhydrous choline chloride single crystal;

FIG. 3 XRD of anhydrous choline chloride single crystal;

FIG. 4 XRD of anhydrous choline chloride single crystal and commercial choline chloride;

FIG. 5 TG of anhydrous choline chloride single crystal and commercial choline chloride;

EXPERIMENT EXAMPLES

The invention is further illustrated by the following examples, which are intended to provide a better understanding of the invention. However, the examples do not limit the scope of the invention in any way. Improvements and modifications made by those technical staff within the scope within the claims of the present invention are also within the scope of the present invention.

Experiment Example 1

Preparation of Single Crystal from Choline Halide and Alcohol-Ether Compound 17.13 g commercial choline halide and 17.13 g ethylene glycol monomethyl ether were weighed precisely, and added into a reactor with stirring. The reactor was heated to 90° C. The reaction lasts until the homogeneous liquid phase (deep eutectic solvent, DES) was formed. After keeping the reactor at 90° C. for 50 min, the DES product was cooled to 15° C. according to the designed cooling program, and then maintained at 15° C. for a period of time until no more single crystals was precipitated. The cooling program was as follows: 0.5° C./min in the range of 90~70° C., 0.9° C./min in the range of 70~55° C., and 1.2° C./min in the range of 55~15° C. After filtration, washing, and vacuum drying, anhydrous choline halide single crystal was obtained. The entire crystallization experiment took about 1.5 hours, and the filtered mother liquor could be reused. The obtained anhydrous choline chloride single crystal was not agglomerated after being placed in the air for 24 hours, and the water absorption amount was 2.58 wt %, which was much lower than that of commercial choline halide with water absorption amount of 21.86 wt %.

Experiment Example 2

Preparation of Single Crystal from Choline Halide and Mixture of Alcohol-Ether Compound and Polyol 13.9 g commercial choline halide, 18.03 g propylene glycol monomethyl ether and 16.28 g ethylene glycol were weighed precisely, and added into a reactor with stirring. The reactor was heated to 80° C. The reaction lasts until the homogeneous liquid phase (DES) was formed. After keeping the reactor at 80° C. for 50 min, the DES product was cooled to 15° C. according to the designed cooling program, and then maintained at 15° C. for a period of time until no more single crystals were precipitated. The cooling program was as follows: 0.2° C./min in the range of 80~70° C., 0.9° C./min in the range of 70~55° C., and 1.2° C./min in the range of 55~15° C. After filtration, washing, and vacuum drying, anhydrous choline halide single crystal was obtained. The entire crystallization experiment took about 2.0 hours, and the filtered mother liquor could be reused. The obtained anhydrous choline halide single crystal was not agglomerated after being placed in the air for 24 hours, and the water absorption amount was 0.83 wt %, which was much lower than that of commercial choline halide with water absorption amount of 21.86 wt %.

Experiment Example 3

Preparation of Single Crystal from Acetylcholine Chloride and Alcohol-Ether Compound 18.17 g commercial acetylcholine chloride and 18.67 g ethylene glycol monomethyl ether were weighed precisely, and added into a reactor with stirring. The reactor was heated to 75° C. The reaction lasts until the homogeneous liquid phase (DES) was formed. After keeping the reactor at 75° C. for 50 min, the DES product was cooled to 15° C. according to the designed cooling program, and then maintained at 15° C. for a period of time until no more single crystals was precipitated. The cooling program was as follows: 0.6° C./min in the range of 75~70° C., 0.9° C./min in the range of 70~55° C., and 1.2° C./min in the range of 55~15° C. After filtration, washing, and vacuum drying, anhydrous choline halide single crystal was obtained. The entire crystallization experiment took about 3.0 hours, and the filtered mother liquor could be reused. The obtained anhydrous acetylcholine chloride single crystal was not agglomerated after being placed in the air for 24 hours, and the water absorption amount was 1.58 wt %, which was much lower than that of commercial choline halide with water absorption amount of 18.44 wt %.

Experiment Example 4

Preparation of Single Crystal from Propionylcholine Chloride and Mixture of Alcohol-Ether Compound and Polyol 18.17 g commercial propionylcholine chloride, 18.67 g ethylene glycol monomethyl ether and 15.80 g glycerol were weighed precisely, and added into a reactor with stirring. The reactor was heated to 85° C. The reaction lasts until the homogeneous liquid phase (DES) was formed. After keeping the reactor at 85° C. for 50 min, the DES product was cooled to 15° C. according to the designed cooling program, and then maintained at 15° C. for a period of time until no more single crystals was precipitated. The cooling program was as follows: 0.5° C./min in the range of 85~70° C., 0.6° C./min in the range of 70~55° C., and 1.2° C./min in the range of 55~15° C. After filtration, washing, and vacuum drying, anhydrous choline halide single crystal was obtained. The entire crystallization experiment took about 1.0 hours, and the filtered mother liquor could be reused. The obtained anhydrous propionylcholine chloride single crystal was not agglomerated after being placed in the air for 24 hours, and the water absorption amount was 1.06 wt %, which was much lower than that of commercial choline halide with water absorption amount of 15.92 wt %.

Experiment Example 5

Preparation of Single Crystal from Propionylcholine Bromide and Mixture of Alcohol-Ether Compound and Polyol 20.35 g commercial propionylcholine bromide, 16.80 g ethylene glycol monomethyl ether and 16.80 g glycerol were weighed precisely, and added into a reactor with stirring. The reactor was heated to 70° C. The reaction lasts until the homogeneous liquid phase (DES) was formed. After keeping the reactor at 70° C. for 50 min, the DES product was cooled to 15° C. according to the designed cooling program, and then maintained at 15° C. for a period of time until no more single crystal was precipitated. The cooling program was as follows: 1.2° C./min in the range of 70~55° C., and 1.2° C./min in the range of 55~15° C. After filtration, washing, and vacuum drying, anhydrous choline halide single crystal was obtained. The entire crystallization experiment took about 1.5 hours, and the filtered mother liquor could be reused. The obtained anhydrous propionylcholine bromide single crystal was not agglomerated after being placed in the air for 24 hours, and the water absorption amount was 0.77 wt %, which was much lower than that of commercial choline halide with water absorption amount of 16.55 wt %.

Experiment Example 6

25.10 g commercial choline iodide and 18.40 g propylene glycol monomethyl ether were weighed precisely, and added into a reactor with stirring. The reactor was heated to 90° C. The reaction lasts until the homogeneous liquid phase (DES) was formed. After keeping the reactor at 90° C. for 50 min, the DES product was cooled to 15° C. according to the designed cooling program, and then maintained at 15° C. for a period of time until no more single crystal was precipitated. The cooling program was as follows: 0.5° C./min in the range of 90~70° C., 0.9° C./min in the range of 70~55° C., and 1.5° C./min in the range of 55~15° C. After filtration, washing, and vacuum drying, anhydrous choline halide single crystal was obtained. The entire crystallization experiment took about 1.5 hours, and the filtered mother liquor could be reused. The obtained anhydrous choline iodide single crystal was not agglomerated after being placed in the air for 24 hours, and the water absorption amount was 2.30 wt %, which was much lower than that of commercial choline halide with water absorption amount of 20.10 wt %.

The crystal structure and thermal stability of anhydrous choline chloride single crystal product obtained in Experiment example 1 were analyzed, respectively.

FIGS. 1 and 2 show the diffraction structure and cell diagram of anhydrous choline chloride single crystal obtained in Experiment example 1. The final reliability factor of the single crystal product is R1=0.0248, wR2=0.0861. The highest peak and the lowest peak on the difference Fourier diagram are 0.306 and −0.278e/Å 3, respectively.

Each single crystal unit cell includes four molecules of choline chloride. The single crystal data are shown in Table 1.

TABLE 1

| Single crystal data of anhydrous choline halide | |
|---|---|
| Identification code | b |
| Empirical formula | $C_5 H_{14} Cl N O$ |
| Formula weight | 139.62 |
| Temperature | 386(2) K |
| Wavelength | 0.71073 Å |
| Crystal system, space group | orthorhombic system, P $2_1 2_1 2_1$ |
| Unit cell dimensions | a = 5.8717(7) Å  alpha = 90 deg. |
| | b = 11.0472(12) Å  beta = 90 deg. |
| | c = 11.5966(12) Å  gamma = 90 deg. |
| Volume | 752.22(14) Å$^3$ |
| Z, Calculated density | 4, 1.233 Mg/m$^3$ |
| Absorption coefficient | 0.423 mm$^{-1}$ |
| F(000) | 304 |
| Crystal size | 0.20 × 0.15 × 0.10 mm |
| Theta range for data collection | 3.51 to 27.51 deg. |
| Limiting indices | −7 <= h <= 7, −14 <= k <= 14, −15 <= l <= 9 |
| Reflections collected/unique | 7697/1722 [R(int) = 0.0219] |
| Completeness to theta = 27.51 | 99.7% |
| Max. and min. transmission | 0.9589 and 0.9201 |
| Refinement method | Full-matrix least-squares on F$^2$ |
| Data/restraints/parameters | 1722/0/74 |
| Goodness-of-fit on F$^2$ | 1.013 |
| Final R indices [I > 2sigma(I)] | R1 = 0.0248, wR2 = 0.0861 |
| R indices (all data) | R1 = 0.0253, wR2 = 0.0873 |
| Absolute structure parameter | −0.07(6) |
| Extinction coefficient | 0.028(8) |
| Largest diff. peak and hole | 0.306 and −0.278 e · Å$^{-3}$ |

FIG. 2 is X-ray powder diffraction pattern of anhydrous choline chloride single crystal product obtained in Experiment example 1. FIG. 4 is an X-ray powder diffraction comparison between commercial choline chloride and the anhydrous choline chloride obtained in Experiment example 1. It can be confirmed that the obtained product is obviously different from the commercial choline chloride. The spectrum of the obtained product has sharp and clearly peak, and the product is high-quality single crystal product.

FIG. 5 is thermodynamic stability comparison between commercial choline chloride and the anhydrous choline chloride obtained in Experiment example 1.

At 330° C., the product and commercial choline chloride began to lose weight due to the evaporation of water. In the range of 330° C.~370° C., they began to be thermally cracked, thus weight loss could be observed obviously in the spectrum.

The initial temperature of thermal cracking of anhydrous choline chloride single crystal is 350° C., and the weight loss rate reaches the maximum at 370° C. The initial temperature of commercial choline chloride is 330° C., and the weight loss rate reaches the maximum at 350° C. The results of thermogravimetric analysis show that the thermal stability of anhydrous choline chloride single crystal is better than that of commercial choline chloride.

It can be concluded from FIGS. 1-5 that the product prepared in Experiment example 1 is anhydrous choline chloride single crystal, and the single crystal product prepared according to the present invention has the advantages of high quality and good thermal stability. The quality and thermal stability of the single crystal products obtained in other experiment examples are also superior to those of the commercial products obviously according to the results.

With the experiment examples 1-6, it proves the single crystal product has good stability of light and heat. It also has the advantages of moisture resistant, deliquescent resistance and is not easy to agglomerate. The production process is simple in operation which greatly reduces the cost of production. The solvent used in the process is difficult to volatilize and can be recycled. In summary, the invention provides a new method to prepare anhydrous choline halide single crystal and its derivative. It has good economic, environmental and social benefits.

The invention claimed is:

1. A method for preparing anhydrous choline halide single crystal and its derivatives, comprising the steps of:
   (1) Adding an alcohol-ether compound or mixture of an alcohol-ether compound and a polyol to a reactor with stirring, and heating the compound or mixture to 70~90° C.;
   (2) Adding a weighted quantity of choline halide or its derivative, alcohol-ether compound or mixture of alcohol-ether compound and polyol at an optimal molar ratio, to the reaction and continuing to heat and stir until a homogeneous liquid phase product is formed;
   (3) Cooling the product of step (2) to 15° C., and maintaining the product at 15° C. for a period of time until no more single crystal is precipitated; and
   (4) Filtering, washing, and vacuum drying the product of step (3) to obtain anhydrous choline halide single crystal product or a derivative thereof.

2. The method of claim 1, wherein the anhydrous choline halide single crystal product obtained has a formula: $R_1R_2R_3NCH_2CH_2OR_4^+X^-$, wherein $R_1$ is methyl or ethyl, $R_2$ is methyl or ethyl group, $R_3$ is a methyl, ethyl, propyl or butyl group, $R_4$ is hydrogen, acetyl, propionyl or butyryl group, and X is chlorine, bromine or iodine.

3. The method of claim 1, wherein the alcohol-ether compound used has a formula:
   $HO(CH_2)_nOR$ or its isomer, wherein n is an integer of 1 to 10, and R is a methyl, ethyl, propyl, or butyl group.

4. The method of claim 1, wherein the polyol used has a formula:
   $HO(CH_2)_nOR$ or polyethylene glycol, wherein n is an integer of 1 to 10.

5. The method of claim 1, wherein the optimal moral ratio of materials used is $n_{alcohol\text{-}ether\ compound\ or\ mixture\ of\ alcohol\text{-}ether\ compound\ and\ polyol} : n_{choline\ halide\ or\ its\ derivative} = 1:3$.

6. The method of claim 1, wherein the optimal moral ratio of the mixture of alcohol-ether compound and polyol used is $n_{alcohol\text{-}ether\ compound} : n_{polyol} = 1:3$.

7. The method of claim 1, wherein the reaction is conducted for 40~90 min.

8. The method of claim 1, wherein the cooling in the step (3) is controlled by cooling program, and is reduced 0.2 to 0.6° C./min in the range of 90 to 70° C., 0.6 to 1.2° C./min in the range of 70 to 55° C., and 1.2~1.5° C./min the range of 55 to 15° C.

9. The method of claim 8, wherein the temperature is reduced 0.5° C./min in the range of 90 to 70° C., 0.9° C./min in the range of 70 to 55° C., and 1.2° C./min the range of 55 to 15° C.

* * * * *